United States Patent
Musa

(10) Patent No.: US 9,334,236 B2
(45) Date of Patent: May 10, 2016

(54) LACTAM-BASED COMPOUNDS WITH A URETHANE OR UREA FUNCTIONAL GROUP, AND USES THEREOF

(75) Inventor: Osama M. Musa, Kinnelon, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 802 days.

(21) Appl. No.: 13/390,852

(22) PCT Filed: Aug. 18, 2010

(86) PCT No.: PCT/US2010/045842
§ 371 (c)(1),
(2), (4) Date: Feb. 16, 2012

(87) PCT Pub. No.: WO2011/022457
PCT Pub. Date: Feb. 24, 2011

(65) Prior Publication Data
US 2012/0149861 A1    Jun. 14, 2012

Related U.S. Application Data

(60) Provisional application No. 61/234,875, filed on Aug. 18, 2009.

(51) Int. Cl.
| | |
|---|---|
| *C08F 126/10* | (2006.01) |
| *C07D 223/10* | (2006.01) |
| *C08F 226/10* | (2006.01) |
| *C07D 207/12* | (2006.01) |
| *C07D 207/27* | (2006.01) |
| *C08G 18/28* | (2006.01) |
| *C08G 18/81* | (2006.01) |

(52) U.S. Cl.
CPC ............ *C07D 207/27* (2013.01); *C07D 223/10* (2013.01); *C08G 18/2855* (2013.01); *C08G 18/8108* (2013.01)

(58) Field of Classification Search
CPC ............... C07D 207/27; C07D 223/10; G08G 18/2855; G08G 18/8108
USPC ..................... 526/264, 262; 540/531; 548/550
See application file for complete search history.

(56) References Cited

U.S. PATENT DOCUMENTS

| | | | |
|---|---|---|---|
| 4,182,715 A | 1/1980 | Heiba et al. | |
| 4,760,152 A | 7/1988 | Tracy et al. | |
| 5,252,689 A | 10/1993 | Lucas et al. | |
| 5,830,964 A * | 11/1998 | Liu et al. | 526/264 |
| 6,630,599 B1 * | 10/2003 | Singh et al. | 560/25 |
| 2004/0024099 A1 | 2/2004 | Narayanan et al. | |

OTHER PUBLICATIONS

Kadykov et al. ("Synthesis and properties of film-forming caprolactam urethane methacrylate", Khimicheskaya Promyshlennost (Moscow, Russian Federation) (1982), (4), 209-10).*
Seymore/Carraher's Polymer Chemistry, Seventh Edition, 2006, Taylor & Francis Group, Chapter 7, p. 1 and 2.*

* cited by examiner

*Primary Examiner* — Ling Choi
*Assistant Examiner* — Chun-Cheng Wang
(74) *Attorney, Agent, or Firm* — William J. Davis

(57) ABSTRACT

Compounds comprising a lactam moiety, and a urethane or urea functional group are presented. By a preferred synthesis route, they are prepared using at least one polymerizable compound comprising an isocyanate moiety and reacting it with at least one hydroxyalkyl lactam compound or one aminoalkyl lactam compound. In preferred embodiments the lactam moiety is a pyrrolidone or caprolactam ring, and the polymerizable compound is a functionalized aryl isocyanate. The compounds and homopolymers and non-homopolymers thereof find useful application in a wide variety of arts, including: adhesive, agricultural, biocides, cleaning, coating, electronics, encapsulation, membrane, microelectronics, oilfield, performance chemical, personal care, sealant, and sensor applications.

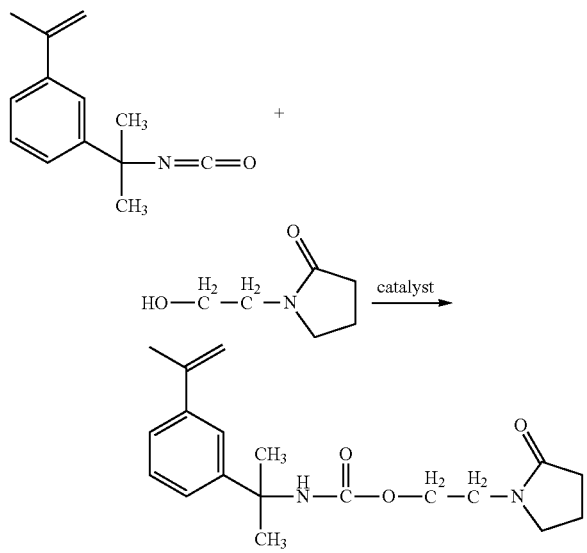

10 Claims, No Drawings

LACTAM-BASED COMPOUNDS WITH A URETHANE OR UREA FUNCTIONAL GROUP, AND USES THEREOF

CROSS REFERENCE TO RELATED APPLICATIONS

This application is the national stage of the PCT Application No. PCT/US2010/045842 filed Aug. 18, 2010, which claims priority from U.S. Provisional Patent Application No. 61/234,875 filed Aug. 18, 2009, the entire disclosures of which are hereby incorporated in their entirety.

BACKGROUND OF THE INVENTION

1. Field of the Invention

The present invention provides compounds comprising a lactam moiety and a urethane or urea functional group. By a prefer synthesis route, they are prepared using a compound comprising a polymerizable moiety and an isocyanate moiety, and reacting it with a hydroxyalkyl lactam or an aminoalkyl lactam. Such compounds may be converted to a wide variety of homopolymers and non-homopolymers.

Alternatively, compounds of the invention may be prepared by reacting a preformed polymer comprising an isocyanate moiety with a compound comprising a hydroxyalkyl lactam moiety or at least one aminoalkyl lactam moiety.

The compounds of the invention may find useful service in any number of arts, including (but not limited to): adhesive, agricultural, biocides, cleaning, coating, electronics, encapsulation, membrane, microelectronics, oilfield, performance chemical, personal care, sealant, and sensor applications.

2. Description of Related Art

N-vinyl lactam-based polymers are those polymers having a lactam group, such as pyrrolidone or caprolactam, where the lactam nitrogen is directly bonded to the polymer backbone. These polymers, which include poly(N-vinyl-2-pyrrolidone), poly(N-vinyl-ε-caprolactam), and poly(N-vinyl-2-pyrrolidone-co-N-vinyl acetate), are available in a wide range of molecular weight, which allows them to find use in many application arts, e.g., as film formers, protective colloids, and suspending agents, among many other uses. A description of these applications and properties is provided in the technical brochure "PVP Polyvinylpyrrolidone Polymers," published by International Specialty Products, which is incorporated in its entirety by reference.

The success of N-vinyl lactam polymers is attributed in part to the chemical structure of the lactam group. With its lone pair of electrons, the lactam nitrogen can form hydrogen bonds with compounds containing —OH and —NH groups. Such interactions can be manifested in a variety of properties, including adhesion (e.g., glue sticks, hair styling, tablet binder), crystallization inhibitor (e.g., gas hydrates, sucrose solutions), and complexation agent (e.g., dyes, active ingredients).

In addition to the molecular weight, the number of carbon atoms in the lactam ring can be varied. Commonly known lactams include those from three carbon atoms/one nitrogen atom in the ring (propiolactam) up to six carbon atoms/one nitrogen atom in the ring (heptanolactam). Increasing the number of carbon atoms in the ring alters the molecule's water hydrophilicity/hydrophobicity balance. Although both poly(N-vinyl-2-pyrrolidone) and poly(N-vinyl-ε-caprolactam) are water soluble, the former is more hydrophilic, absorbing more water in humid environments than the latter.

However, the available ranges in lactam ring size and polymer molecular weight are insufficient to design new monomers and polymers with truly new functionality. For example, because the nitrogen atom of N-vinyl lactams is directly attached to the polymer backbone without a spacer group, there are limited options to modulate the hydrophilicity/hydrophobicity balance of the molecule, or to alter a relatively high glass transition temperature [e.g., about 180° C. for poly(N-vinyl-2-pyrrolidone)]. A new approach is needed that alters the structure of the N-vinyl lactam structure to facilitate new properties and end applications.

To attain different properties current technology relies on copolymerizing other monomer units together with the N-vinyl lactam unit. Many such non-homopolymers are known, and include those formed with N-vinyl acetate, styrene, dimethylaminoethylmethacrylate, dimethylaminopropylmethacrylamide, acrylic acid, and lauryl methacrylate. A number of properties can be altered through these copolymerizations, including hydrophobicity/hydrophilicity, film formation, flexibility, foaming ability, humidity response, viscosity, gloss, and tack. While copolymerizations produce valuable products, they are, in essence, pursued when the homopolymer cannot provide the desired properties. Desired are new lactam-based monomers and polymers thereof that offer expanded functionality.

In addition to functionality limitations, N-vinyl lactam based polymers require production methods and analytical testing to ensure sufficiently low residual monomer. Needed are next-generation lactam-based compounds that provide new properties and also are free of N-vinyl lactam monomer.

There is a related family of compounds, also based on N-alkyl lactams that help extend lactam moiety, in which an alkyl group is covalently bonded to the lactam nitrogen. Various N-alkyl lactams are known, and include N-methyl-2-pyrrolidone, N-ethyl-2-pyrrolidone, N-hydroxyethyl-2-pyrrolidone, N-cyclohexyl-2-pyrrolidone, N-octyl-2-pyrrolidone, and N-dodecyl-2-pyrrolidone, all of which are offered for commercial sale by International Specialty Products (Wayne, N.J.). Also known is N-hydroxymethyl-2-caprolactam (Benson, 1948). These non-polymeric chemicals find application as solvents, surface tension reducers, and low-foaming surface wetting agents.

The prior art teaches several modified N-vinyl lactams via N-alkyl lactams. These documents include: U.S. Pat. Nos. 2,882,262; 4,008,247; 4,189,601; 4,190,582; 4,191,833; 4,191,834; 4,439,616; 4,609,706; 5,209,347; 5,252,689; 5,466,770; 6,369,163; 6,630,599; and US patent applications: 2007/123,673; and foreign patents: EP385,918; EP550,744; and foreign patent applications: WO91/12243; WO02/42383; WO03/006568; WO2007/051738; WO 2008/098885, WO 2008/098887. Many of these publications describe various esters of N-hydroxyalkyllactams, such as N-hydroxyethylpyrrolidone. However, the compositions disclosed in the present invention have not been taught.

Also related is U.S. Pat. No. 6,630,599, which describes hydroxy-, amino-, lactam-, or cyclic urea-blocked derivatives of m- or p-isopropenyl-α,α-dimethylbenzyl isocyanates. These blocked derivatives of isopropenyl-α,α-dimethylbenzyl isocyanate include compounds of the general structure:

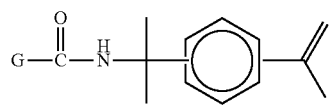

wherein G is:

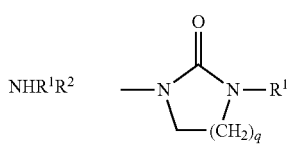

-continued

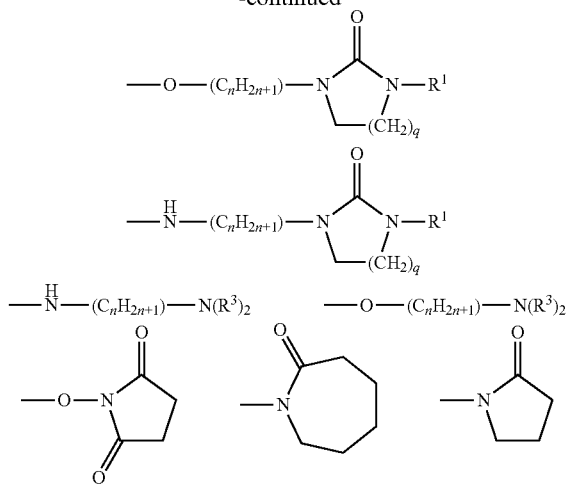

wherein $R^1$ or $R^2$ is, individually, H or a $C_1$-$C_4$ alkyl, n is an integer of from 2 to 4, inclusive, q is 1 or 2, and $R^3$ is a $C_1$-$C_4$ alkyl.

SUMMARY OF THE INVENTION

New lactam-based compounds have been discovered that provide a multitude of functional design options to create new monomers and polymers thereof. These new compounds comprise a lactam moiety, and a urethane or urea functional group. In a first embodiment their generic structure is represented as:

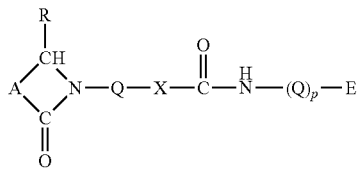

wherein

A is an alkyl or alkenyl group comprising 2 to 50 carbon atoms, wherein 2 to 4 carbon atoms reside in the lactam ring between the

group and the

group;

E is a polymerizable moiety selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and mixtures thereof;

p is 0 or 1;

Q is a spacer group independently selected from the group consisting of functionalized and unfunctionalized alkyl, cycloalkyl, alkenyl, and aryl groups, wherein any of the aforementioned groups may be with or without heteroatoms;

R is independently selected from the group consisting of hydrogen and functionalized and unfunctionalized alkyl, cycloalkyl, alkenyl, and aryl groups, wherein any of the beforementioned groups may be with or without heteroatoms; and —X— is selected from the group consisting of —O— and

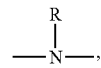

wherein R retains its definition of this section.

Alternatively, compounds of the invention may be represented by a second generic structure:

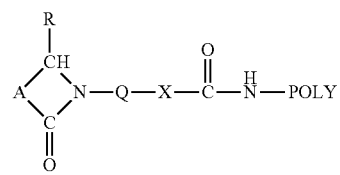

wherein A, Q, R, and —X— retain their definitions provided for the first generic structure above, and the group POLY represents any polymeric entity, wherein the lactam urethane and/or lactam urea occurs along the polymer chain, on an end group, or on a pendant chain. The polymer represented by the second generic structure may be a random, blocked, or alternating polymer of linear or branched arrangement.

These new lactam-based compounds, and the homopolymers and non-homopolymers thereof find broad application in numerous application areas, including the adhesive, agricultural, biocides, cleaning, coating, electronics, encapsulation, membrane, microelectronics, oilfield, performance chemical, personal care, sealant, and sensor applications.

DETAILED DESCRIPTION OF THE INVENTION

The present invention describes an entirely new class of compounds based on lactam chemistry that resolve problems noted with existing N-vinyl lactams, affording new properties that have not been possible with N-vinyl lactam polymers. These new compounds comprise a lactam ring and a variable spacer group based on hydroxyalkyl and aminoalkyl chemistries between the nitrogen lactam and a polymerizable moiety or a polymer. These new compounds and the polymers produced therefrom find application in a wide variety of useful applications, including (but not limited to): adhesive, agricultural, biocides, cleaning, coating, electronics, encapsulation, membrane, microelectronics, oilfield, performance chemical, personal care, sealant, and sensor applications.

As used herein, the following terms have the meanings set out below:

The term direct bond means that the group can be nothing.

The term halogen refers to chloro, bromo, iodo and fluoro, and is preferably bromo or chloro.

The term heteroatom refers to atoms such as oxygen, nitrogen, sulfur, and phosphorus.

The symbol of a bond to the middle of a vinyl group means that the bond can be attached to either side of the vinyl group and means that the structure is referring to a mixture of isomers. For example, in the structure below:

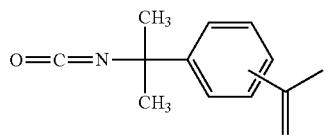

the vinyl group can be attached to either the meta or para position of the ring structure.

The term small molecule refers to two or more atoms held together by covalent bonds, typically with a molecular weight less than about 2000 atomic mass units (amu).

The term monomer refers to the repeat units that comprise a polymer. A monomer is a compound that chemically bonds to other molecules, including other monomers, to form a polymer.

The terms polymer refers to a molecule comprising multiple monomer units connected by covalent chemical bonds. By this definition polymer encompasses molecules wherein the number of monomer units ranges from very few, which more commonly may be called oligomers, to very many.

The term macromolecule refers to any large molecule, which includes polymers.

The term homopolymer refers to a molecule that comprises a single monomer, and includes such polymers wherein a small amount of polymerization solvent may be covalently bonded into the polymer.

The term non-homopolymer refers to a molecule that comprises two or more different monomers. Nonlimiting examples of non-homopolymers include copolymers, terpolymers, tetramers, and the like, wherein the non-homopolymer is a random, blocked, or alternating polymer.

The term biomolecule refers to any molecule produced by a living organism (and their synthetic analogues), and includes subcategories such as small molecules (e.g., carbohydrates, lipids, hormones), monomers (e.g., amino acids, monosaccharides), oligomers (e.g., fats and oils) polymers (e.g., polysaccharides, lignin, proteins), and macromolecules (e.g., polypeptides).

The term branched refers to any non-linear molecular structure. To avoid any arbitrary delineation, the term branched describes both branched and hyperbranched structures.

The term free radical addition polymerization initiator refers to a compound used in a catalytic amount to initiate a free radical addition polymerization. The choice of initiator depends mainly upon its solubility and its decomposition temperature.

The term inert solvent refers to a solvent that does not interfere chemically with the reaction.

The term personal care composition refers to such illustrative non-limiting compositions as skin, sun, oil, hair, cosmetic, and preservative compositions, including those to alter the color and appearance of the skin. Potential personal care compositions include, but are not limited to, polymers for increased flexibility in styling, durable styling, increased humidity resistance for hair, skin, and color cosmetics, sun care water-proof/resistance, wear-resistance, and thermal protecting/enhancing compositions.

The term performance chemicals composition refers to non-personal care compositions that serve a broad variety of applications, and include nonlimiting compositions such as: adhesives; agricultural, biocides, coatings, electronics, household-industrial-institutional (HI&I), inks, membranes, metal fluids, oilfield, paper, paints, plastics, printing, plasters, and wood-care compositions.

All percentages, ratio, and proportions used herein are based on a weight basis unless otherwise specified.

Description of the Compounds

The discovered compounds that resolve the problems noted with existing N-vinyl lactam compounds are those that comprise a lactam moiety, a urethane or urea functional group, and a polymerizable moiety. One representation of their generic structure is:

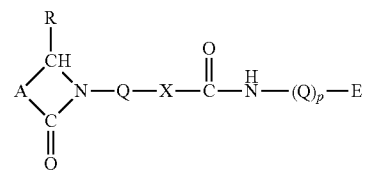

(1)

Each of the follow generalized groups, A, E, p, Q, R, and —X—, in the above structure will be defined, with preferred (but non-limiting examples) provided for each.

The linker group —X— is selected from the group consisting of —O— and

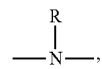

wherein R will be defined later. As it will be discussed in greater detail in the Synthesis section, the linker group represents the reactive union of parent reactants, e.g., an isocyanate-containing compound with a hydroxyalkyl lactam compound or an aminoalkyl lactam compound. With this definition of the linker group, the invention's compounds will be recognized as being urethanes:

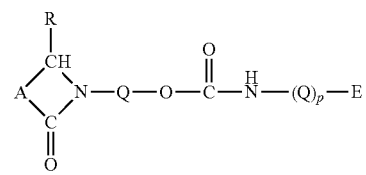

(2)

or ureas:

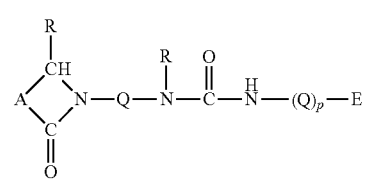

(3)

The group A represents an alkyl or alkenyl group comprising 2 to 50 carbon atoms, wherein 2 to 4 carbon atoms reside in the lactam ring between the

group and the

group. Many specific examples of A exist and are within the scope of the invention. In preferred embodiments -A- groups that may reside in the lactam ring between the

group and the

group include:

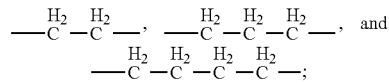

the formed lactam rings are pyrrolidone, piperidone, and caprolactam, respectively. Other members of the -A- group can be made by one skilled in the art without departing from the spirit of the current invention.

The E group is a polymerizable moiety selected from the group consisting of: acrylamides, acrylates, allyl derivatives, anhydrides, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and blends thereof.

Referring back to structure (1), the subscript p is selected from the group consisting of 0 and 1. When p equals 0, then a direct bond exists between the polymerizable moiety E and the urethane/urea nitrogen. Otherwise, when p equals unity then a spacer group Q exists between these two groups. Furthermore, when p equals unity it is noted that the two spacer groups Q in structures (1), (2), and (3) may be independently selected from each other.

The spacer group Q is independently selected from the group consisting of functionalized and unfunctionalized alkyl, cycloalkyl, alkenyl, and aryl groups, wherein any of the aforementioned groups may exist with or without heteroatoms.

Mentioned earlier, R is independently selected from the group consisting of hydrogen, and functionalized and unfunctionalized alkyl, cycloalkyl, alkenyl, and aryl groups, wherein any of the beforementioned groups may be with or without heteroatoms.

In preferred embodiments, A is selected from the group consisting of

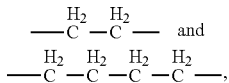

meaning that the lactam ring is pyrrolidone and caprolactam, respectively. Thus, preferred urethane structures (2) are:

(4)

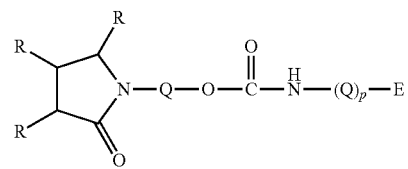

(5)

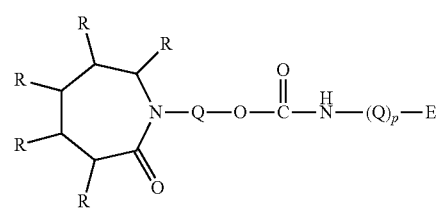

and preferred urea structures (3) are:

(6)

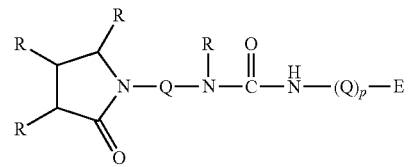

(7)

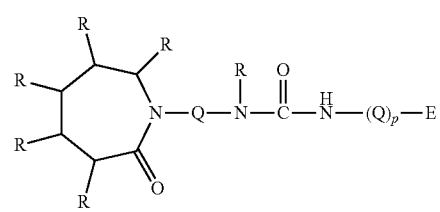

wherein the groups E, p, Q and R retain their earlier definitions.

By defining preferred examples for the remaining groups, many compounds can be identified. Non-limiting examples of these molecules now will be given, with the understanding that one skilled in the art can identify additional A, E, p, Q, and R groups and thereby construct additional compounds that remains within the spirit and scope of the invention.

While E retains its earlier definition, in preferred embodiments E is selected from the group consisting of: styrenes.

While Q retains its earlier definition, in preferred embodiments Q is selected from the group consisting of: aryl, functionalized aryl, methyl, ethyl, and propyl.

While R retains its earlier definition, in preferred embodiments R is hydrogen.

Within these preferred descriptions, preferred compounds of structures (4), (5), (6) and (7) that are embraced by the invention are:

urethane structures:

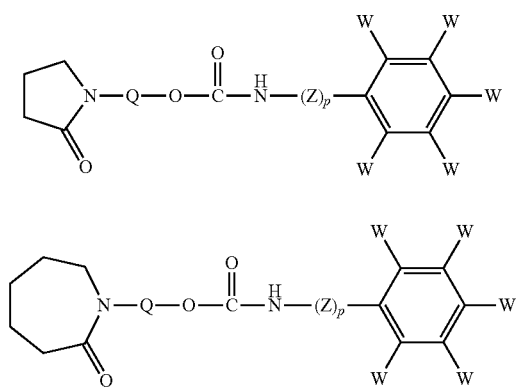

and urea structures:

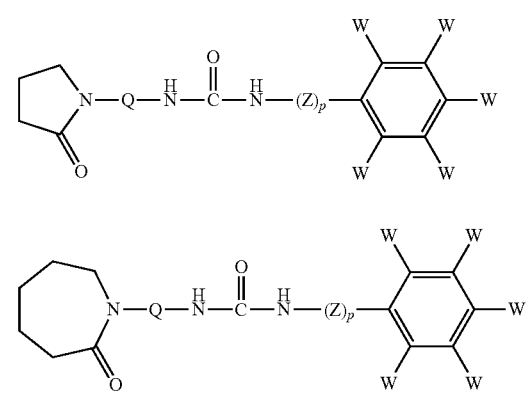

wherein p and Q retain their earlier definitions, and each W is independently selected from the group consisting of vinyl and allyl derivatives, and the spacer group Z represents an alkyl group.

Preferred embodiments of the remaining groups can be now provided. Highly preferred compounds of the invention include:

methyl urethanes:

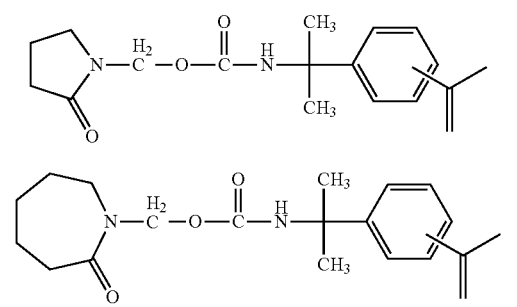

ethyl urethanes:

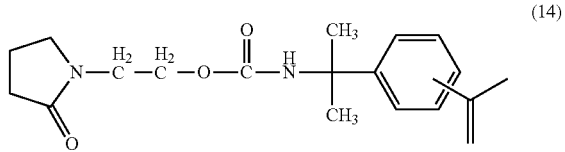

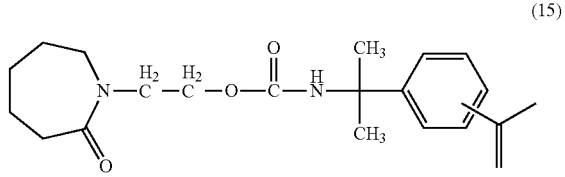

propyl urethanes:

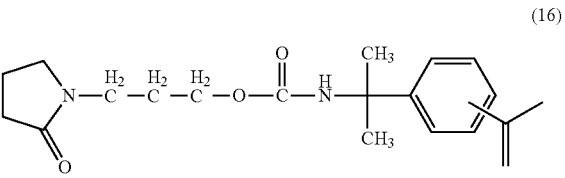

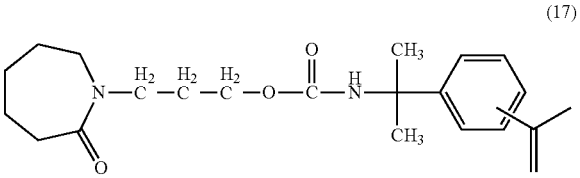

methyl ureas:

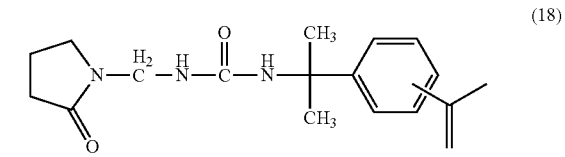

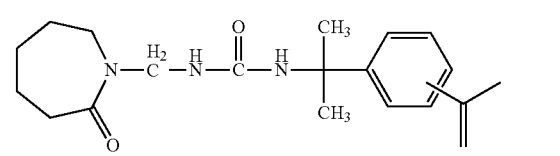

ethyl ureas:

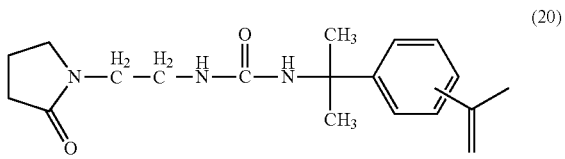

-continued propyl ureas:

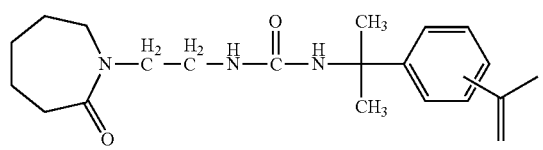
(21)

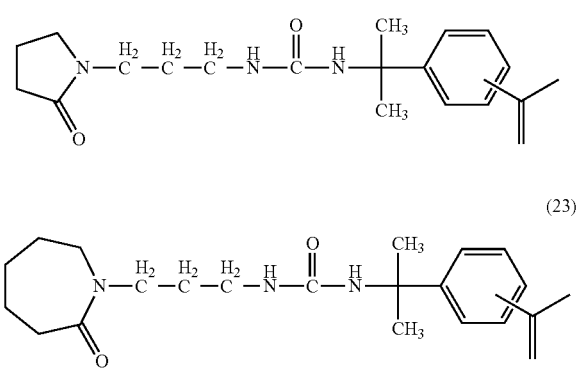
(22)

(23)

As mentioned in the beginning of this section, structure (1) represents one generic structure of the invention's compounds. A second depiction of the invention's compounds can be made:

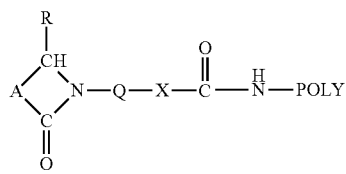
(24)

The group A represents an alkyl or alkenyl group comprising 2 to 50 carbon atoms, wherein 2 to 4 carbon atoms reside in the lactam ring between the

group and the

group. Many specific examples of A exist and are within the scope of the invention. In preferred embodiments -A- groups that may reside in the lactam ring between the

group and the

group include:

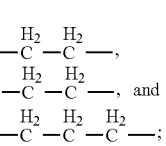

the formed lactam groups are pyrrolidone, piperidone, and caprolactam, respectively. Other members of the -A- group can be made by one skilled in the art without departing from the spirit of the current invention.

The linker group —X— is selected from the group consisting of —O— and

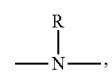

wherein R will be defined later. As it will be discussed in greater detail in the Synthesis section, the linker group represents the reactive union of parent reactants, e.g., an isocyanate-containing polymer with a hydroxyalkyl lactam compound or an aminoalkyl lactam compound.

The spacer group Q is independently selected from the group consisting of functionalized and unfunctionalized alkyl, cycloalkyl, alkenyl, and aryl groups, wherein any of the aforementioned groups may exist with or without heteroatoms.

R is independently selected from the group consisting of hydrogen, and functionalized and unfunctionalized alkyl, cycloalkyl, alkenyl, and aryl groups, wherein any of the beforementioned groups may be with or without heteroatoms.

The group POLY of structure (24) represents any polymeric entity, wherein the lactam urethane and/or lactam urea occurs along the polymer chain, on an end group, or on a pendant chain. The polymer represented by structure (24) may be a random, blocked, or alternating polymer of linear or branched arrangement.

Synthesis of the Lactam-Based Compounds

Generally speaking, there are two synthesis approaches by which compounds of this invention may be produced. The first approach is characterized by the use of a polymerizable reactant having at least one isocyanate moiety, and is the preferred synthesis approach. Alternatively, a second approach may be employed, in which a preformed polymer having at least one isocyanate moiety is a reacted, instead of the polymerizable isocyanate compound.

A description now will be provided for the first synthesis approach. The urethane compounds represented by structure (2) may be derived from a reaction comprising a polymerizable isocyanate reactant (which will be discussed later) and a hydroxyalkyl lactam, which has the generic structure:

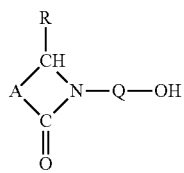
(25)

wherein A represents an alkyl or alkenyl group comprising 2 to 50 carbon atoms, wherein 2 to 4 carbon atoms reside in the lactam ring between the group and the group. The group Q is selected from the group consisting of functionalized and unfunctionalized alkyl, cycloalkyl, alkenyl, and aryl groups, wherein any of the aforementioned groups may exist with or without heteroatoms. The group R is selected from the group consisting of hydrogen, and functionalized and unfunctionalized alkyl, cycloalkyl, alkenyl, and aryl groups, wherein any of the beforementioned groups may be with or without heteroatoms. retain their earlier definitions. OH is a hydroxyl group.

Preferred examples of hydroxyalkyl lactams having structure (25) include:
N-hydroxymethyl pyrrolidone, which is disclosed in U.S. Pat. No. 2,865,912;
N-hydroxyethyl-2-pyrrolidone, which is sold under the trade name HEP® by International Specialty Products (Wayne, N.J.),
N-hydroxypropyl-2-pyrrolidone, which is disclosed in U.S. Pat. No. 2,865,912;
N-hydroxymethyl-2-piperidone, which is disclosed in U.S. Pat. No. 2,865,912;
N-hydroxyethyl-2-piperidone, which is disclosed in U.S. Pat. No. 2,865,912;
N-hydroxymethyl-2-caprolactam, the synthesis of which is taught in a paper by Benson (1948);
N-hydroxyethyl-2-caprolactam, which is disclosed in U.S. Pat. No. 2,865,912; and
N-(α-hydroxy-β-trichloroethyl) caprolactam, which is disclosed in U.S. Pat. No. 2,865,912.

Similarly, urea compounds represented by structure (3) may be derived from a reaction comprising a polymerizable isocyanate reactant and an aminoalkyl lactam, which have the generic structure:

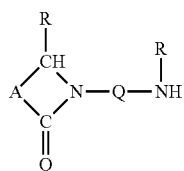
(26)

wherein A represents an alkyl or alkenyl group comprising 2 to 50 carbon atoms, wherein 2 to 4 carbon atoms reside in the lactam ring between the group and the group. The group Q is selected from the group consisting of functionalized and unfunctionalized alkyl, cycloalkyl, alkenyl, and aryl groups, wherein any of the aforementioned groups may exist with or without heteroatoms. Each R group is independently selected from the group consisting of hydrogen, and functionalized and unfunctionalized alkyl, cycloalkyl, alkenyl, and aryl groups, wherein any of the beforementioned groups may be with or without heteroatoms. H is a hydrogen atom.

Preferred examples of aminoalkyl lactams having structure (26) include the analogues of N-hydroxyalkyl lactam, such as:
aminomethyl-2-pyrrolidone,
aminoethyl-2-pyrrolidone,
aminopropyl-2-pyrrolidone,
aminomethyl-2-caprolactam,
aminoethyl-2-caprolactam, and
aminopropyl-2-caprolactam.

The polymerizable isocyanate reactant necessary for both these reactions takes the following generic form:

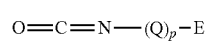
(27)

wherein E is a polymerizable moiety selected from the group consisting of: acrylamides, acrylates, allyl derivatives, anhydrides, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and blends thereof. The subscript p is 0 or 1. Q is selected from the group consisting of functionalized and unfunctionalized alkyl, cycloalkyl, alkenyl, and aryl groups, wherein any of the aforementioned groups may exist with or without heteroatoms.

Without limitation, a preferred group of polymerizable isocyanates are the functionalized aryl isocyanates, which can be represented as:

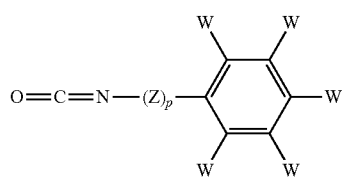
(28)

wherein the subscript p is 0 or 1, each W is independently selected from the group consisting of vinyl derivatives and allyl derivatives, and the spacer group Z represents an alkyl group.

This group of preferred polymerizable isocyanates includes many known compounds, including (without limitation): those taught in U.S. Pat. Nos. 2,468,716; 2,647,884; 3,079,355; and 3,225,119; the contents of which are incorporated herein their entirety by reference, as well as the following known compounds:

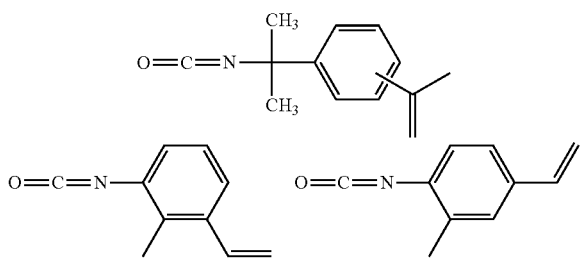

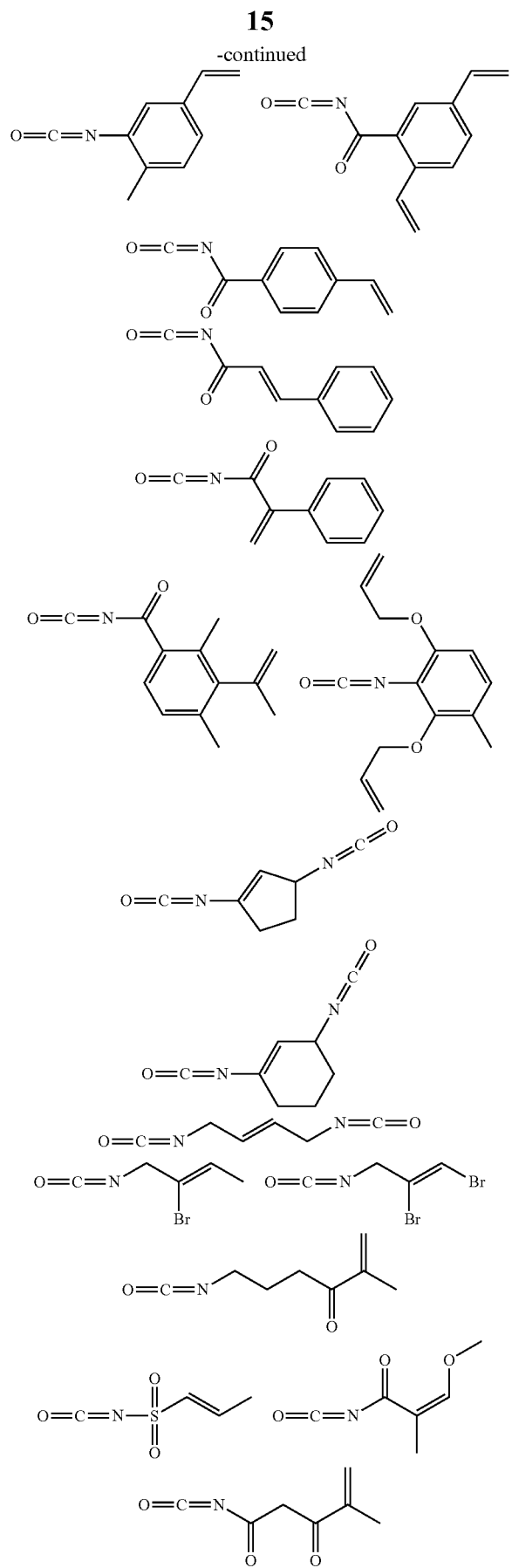
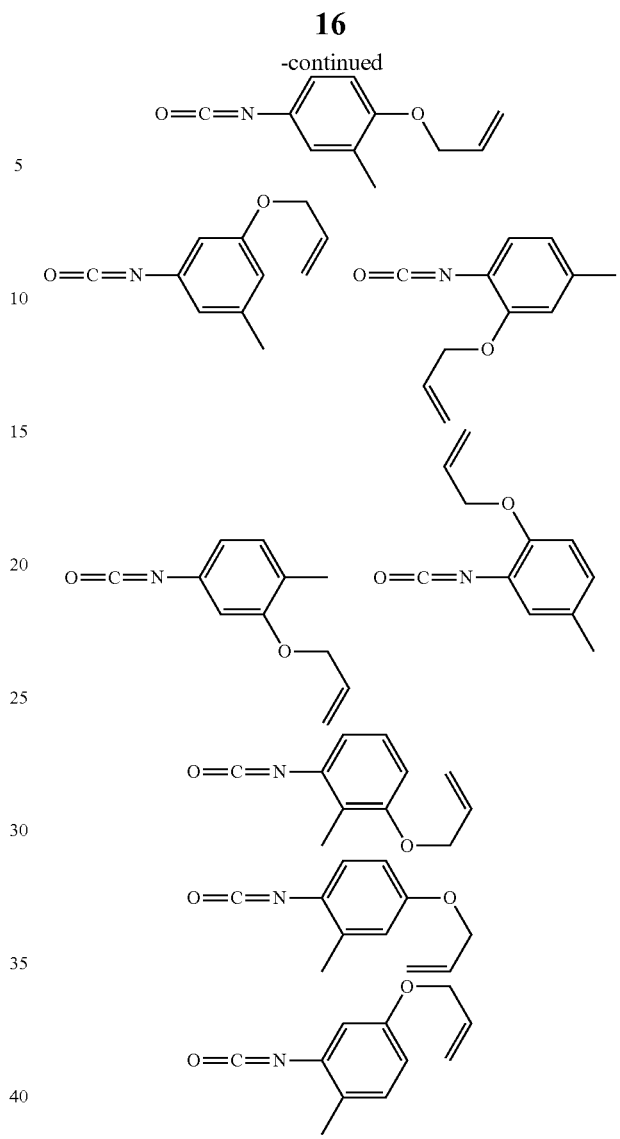

A highly preferred polymerizable isocyanate is represented by the first structure of this group, 3-isopropenyl-α,α-dimethylbenzyl isocyanate, for which both meta and para isomers are known. Cytec Industries, Inc. (West Paterson, N.J.) offers for commercial sale the meta isomer under the trade name TMI®, and it is described in their sales brochure, *TMI® (meta) Unsaturated Aliphatic Isocyanate*, which is hereby incorporated in its entirety by reference. Application areas for 3-isopropenyl-α,α-dimethylbenzyl isocyanate include latex modification, original-equipment-manufacturer (OEM) parts, rheology control agents, plastic modification, macromonomer synthesis, and light-stable coatings.

The description just provided describes compounds of the invention produced via a polymerizable isocyanate, which is a preferred synthesis approach. As mentioned earlier, a second synthesis approach also may be employed, wherein a preformed polymer containing at least one isocyanate moiety is reacted with a hydroxyalkyl lactam of structure (25) or aminoalkyl lactam of structure (26).

Suitable isocyanate-containing polymers are generally well-known to one skilled in the art, as they contain at least one N=C=O functional group, which may occur on the polymer chain, on a pendant group, or on a branch chain. Examples of these polymers include, but are not limited to:

poly(neopentyl glycol adipate) polymer terminated with isophorone diisocyanate; poly(phenyl isocyanate-co-formaldehyde); poly(propylene glycol) terminated with 2,4-diisocyanate tolylene; poly(ethylene adipate) terminated with 2,4-diisocyanate tolylene; poly(neopentyl glycol adipate) terminated with isophorone diisocyanate; poly(1,4-butanediol) terminated with 2,4-diisocyanate tolylene; and mixtures thereof.

An example of structure (24) formed by the reaction of a hydroxyalkyl lactam and a preformed polymer containing at least one isocyanate moiety is:

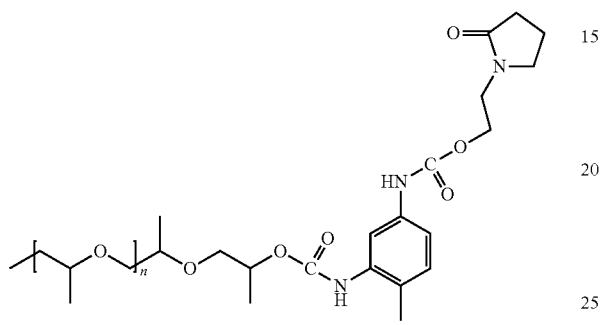

synthesized by reacting N-hydroxyethyl-2-pyrrolidone with poly(propylene glycol) terminated with 2,4-diisocyanate tolylene. Of course, preformed polymers containing more than one isocyanate group may be expected to yield product of the invention with more than one covalently bonded lactam urethane and/or lactam urea moiety.

Also suitable are silane and siloxane isocyanate compounds and polymers, including those of U.S. Pat. Nos. 4,654,428; 4,732,995, for which both are incorporated herein their entirety by reference.

Reactions performed by the first and second approach can be conducted with or without solvent. This second synthesis approach may benefit from the optional addition of an inert solvent when the reactant system viscosity limits effective reactive processing (i.e., has a high viscosity).

A catalyst, such as dibutyltin dilaurate, used in the customary amounts, can be used to alter the reaction rate, e.g., speeding the reaction and/or favoring one product over side products.

Because compounds of this invention comprise a polymerizable group, they are monomers, and are well-suited to be converted to a wide variety of useful polymers, including homopolymers and non-homopolymers. These polymers may be produced using methods known to one skilled in the art Optional Units for Non-Homopolymerization Comonomer unit(s) that may be used for the creation of non-homopolymers include, selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl carbonates, vinyl ethers, vinyl imidazoles, vinyl lactams, vinyl pyridines, vinyl silanes, vinyl sulfones, and mixtures thereof. The non-homopolymer may be a random, blocked, or alternating polymer.

Examples of these comonomer units include, without limitation:

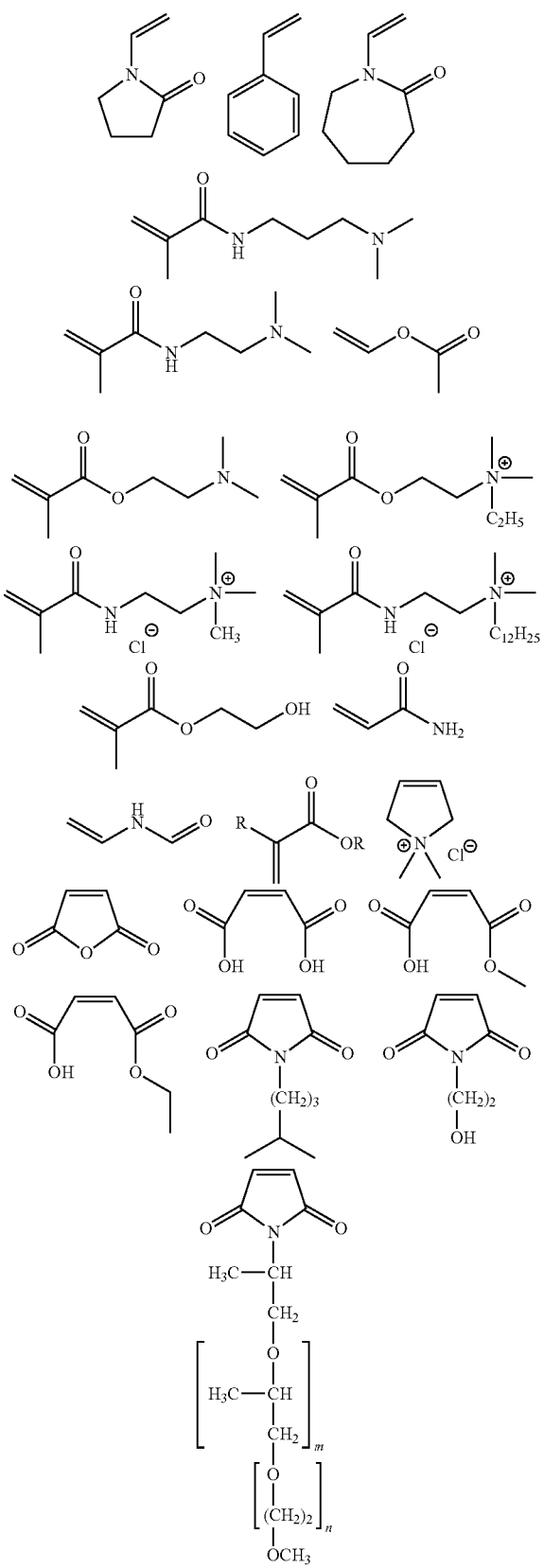

wherein each R is independently selected from the group consisting of hydrogen, and functionalized and unfunctionalized alkyl, cycloalkyl, alkenyl, and aryl groups, wherein any of the beforementioned groups may be with or without heteroatoms, and m and n are integers greater than or equal to 1.

Additionally, preferred comonomer units also include siloxane monomers, which are generally well-known and commercially available. Polysiloxane polymers and films thereof impart a wide variety of functional properties of great commercial value, such as: water repellency to glass, leather, paper, fabric surfaces and powder; environmental, mechanical, and dampening protection for microelectronic devices; release coatings; fabric softening, and adhesion promoters, and for use in the sensor, optoelectronics, and microelectronics industries.

Siloxane monomers are disclosed WO 2004/060975, which is incorporated herein in its entirety by reference, and have the general formula:

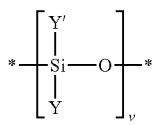

wherein Y' denotes hydrogen or an optionally substituted functional alkyl, alkyl, alkenyl, aryl, alkaryl or aralkyl group having 1 to 20 carbon atoms, Y denotes a substituted alkyl, aryl, alkaryl or aralkyl group having 1 to 20 carbon atoms, and v denotes an integer with values of from 3 to 1000.

The functional alkyl groups can be, for example: chloropropyl, acryloxypropyl and methacryloxypropyl. The alkyl groups can be, for example: methyl, ethyl, n-propyl, trifluoropropyl, n-butyl, see-butyl and t-butyl. The alkenyl groups can be, for example: vinyl, allyl, propenyl, and butenyl. The aryl, alkaryl and aralkyl groups can be, for example, phenyl, tolyl, benzyl and phenypropyl. The preferred groups are hydrogen, methyl, ethyl, phenyl, trifluoropropyl, acryloxyproply, methacryloxypropyl and vinyl. Preferably, the value of v is from 3 to 500, most preferably from 4 to 200.

A (chain) terminating agent or end capper may be used to regulate the degree of polymerization of the polymer and/or to add functionality. Suitable siloxane-terminating agents have the general formula:

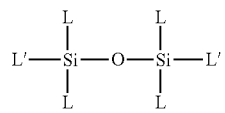

wherein L' denotes hydrogen or an optionally substituted functional alkyl, alkyl, alkenyl, aryl, alkaryl or aralkyl group having 1 to 8 carbon atoms, L denotes substituted alkyl, aryl, alkaryl or aralkyl group having 1 to 8 carbon atoms.

In the terminating agent, the functional alkyl groups can be for example: aminopropyl, acryloxypropyl, methacryloxypropyl, and epoxypropyl. The alkyl groups can be, for example: methyl, ethyl, n-propyl, trifluoropropyl, n-butyl, see-butyl and t-butyl. The alkenyl groups can be, for example: vinyl, allyl, propenyl, and butenyl. The aryl, alkaryl and aralkyl groups can be, for example: phenyl, tolyl, benzyl and phenethyl. The preferred groups are hydrogen, methyl, ethyl, phenyl, trifluoropropyl, acryloxyproply, methacryloxypropyl and vinyl.

Also suitable are the monomers disclosed in US patent application 2007/0204412, which is incorporated herein its entirety by reference. These monomers have the general formula:

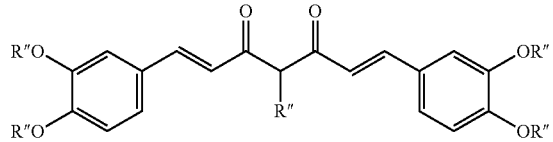

wherein R" is independently selected from the group consisting of hydrogen and branched and straight chain, substituted and unsubstituted groups selected from alkyl, alkenyl, alkoxy and alkenoxy groups of from 1 to about 5 carbon atoms, silane and siloxy groups of from 1 to about 15 carbon and/or silicon atoms in the primary chain, and alkoxysilane and alkenoxysilane groups of from 1 to about 15 carbon and/or silicon atoms in the primary chain.

Such monomers find application in a broad range of applications, including medical and diagnostic devices, and instrumentation and sensors.

Also suitable are vinyl-terminated polydimethylsiloxanes and vinyl-terminated fumed silica reinforced polydimethylsiloxanes, such as those offered into commercial sale by Gelest, Inc. (Morrisville, Pa.), having viscosities ranging from about 0.7 cSt to about 165,000 cSt.

Also suitable are the isocyanate silicones offered for commercial sale by Siltech Corp. of Toronto, ON, CA, and Siltech LLC of Dacula, Ga., US. These isocyanates include Silmer® NCO isocyanate functional pre-polymer, which is available as multi- and linear-difunctional configurations, as well as varying molecular weight.

Applications

The compounds of the invention, homopolymers and non-homopolymers thereof may be used in any useful application. Contemplated is their use in: adhesives and adhesive promoters; antennae for radio-frequency identification (RFID); binders (for wood, rubber, recycled materials, flooring, carpet underlays, moulding for steel casting); circuit board fabrication; coatings (e.g., for steel, concrete, wood, cellulose materials; release coatings); fabric softening; footware (e.g., soles); foam (bedding, car seats, filling material, furniture, headrests, mattresses, pillows, transportation cabin components); elastomers (e.g., rollers, belts, roller blades, printing rollers, hoses); insulation (residential, commercial, institutional constructions); medical and diagnostic devices/instrumentation/sensors; microelectronic devices (e.g., for environmental, mechanical, and dampening protection; and sensors and optoelectronics); rigid insulating foam; sealants; underfill encapsulants; and water repellency (e.g., glass, leather, paper, fabric surfaces, powders)

Characterizing the Reaction Product

The compositions of this invention can be analyzed by known techniques to characterize the product. Especially preferred are the techniques of $^{13}C$ nuclear magnetic resonance (NMR) spectroscopy, gas chromatography (GC), and gel permeation chromatography (GPC) in order to decipher polymer identity, residual monomer concentrations, polymer molecular weight, and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses include the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual monomer levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography*, third edition (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The invention will now be described with reference to the following examples:

EXAMPLES

Example 1

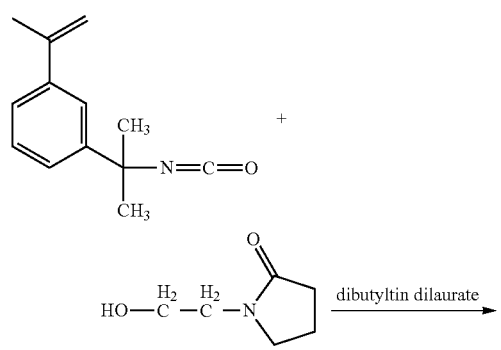

-continued

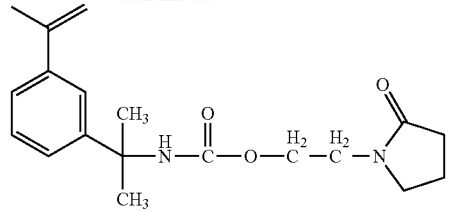

N-hydroxyethyl-2-pyrrolidone (200 g) was added without solvent to a reaction flask equipped with a mechanical mixer, a reflux condenser with bubbler, slow-addition funnel and an oil bath with a temperature probe and controller. A catalytic amount (approximately 2 mL) of dibutyltin dilaurate was added. After the reaction temperature stabilized to within 65° C.-70° C., m-3-isopropenyl-α,α-dimethylbenzyl isocyanate (311.5 g) was added to the flask. The reaction temperature was maintained between 70° C.-75° C. The reaction temperature was maintained 75° C.-80° C. for two hours. Completion of the reaction was evaluated by FT-IR based on the disappearance of the isocyanate peak at λ=2255 cm$^{-1}$. A viscous, clear-gold liquid was discharged from the reaction flask and at room temperature the liquid solidified into an ivory-white solid. Its melting point, as measured by differential scanning calorimetry, was found to be 67° C. Nuclear magnetic resonance (NMR) determined conformance of the product with the above structural form. Product purity of the batches was found to be greater than or equal to 97 mol %.

Example 2

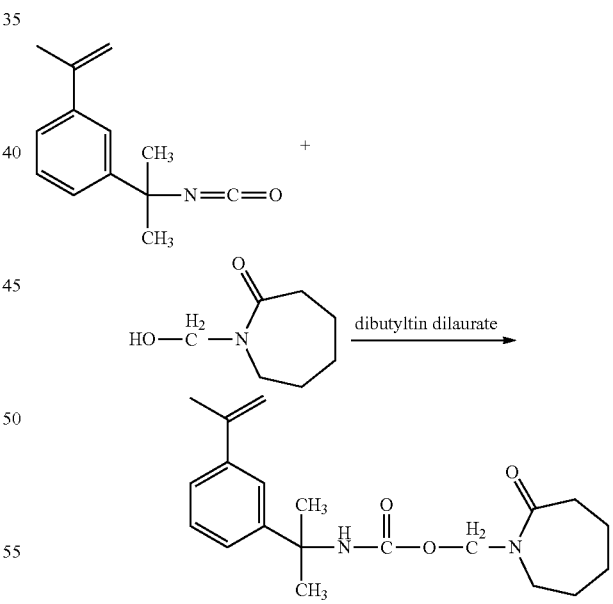

N-hydroxymethyl-2-caprolactam (97%) (30.93 g) was added without solvent to a reaction flask equipped with a mechanical mixer, a reflux condenser with bubbler, slow-addition funnel and an oil bath with a temperature probe and controller. The reaction flask was immersed in the oil bath preheated to a temperature of 70° C. A catalytic amount (approximately 2 mL) of dibutyltin dilaurate was then added to the light grey slurry, After the reaction temperature stabilized to about 75° C., m-3-isopropenyl-α,α-dimethylbenzyl isocyanate (94.3%) (44.8 g) was slowly added to the flask over 50 minutes. An exotherm developed and the reaction temperature was maintained between 75° C.-80° C. During this time, the reaction changed from a very light grey slurry to a thick and foamy white semi-solid. The reaction temperature was maintained at 75° C.-80° C. for about seven hours. After about six hours, 1.0 gram of N-hydroxymethyl-2-caprolactam was added to consume any unreacted m-3-isopropenyl-α,α-dimethylbenzyl isocyanate. Completion of the reaction was monitored by FT-IR based on the disappearance of the isocyanate peak at $\lambda=2255$ cm$^{-1}$. A very viscous, pearl-white liquid was discharged from the reaction flask. NMR determined conformance of the product with the above structural form. Product purity of the batch was found to be 95 mol %.

Example 3

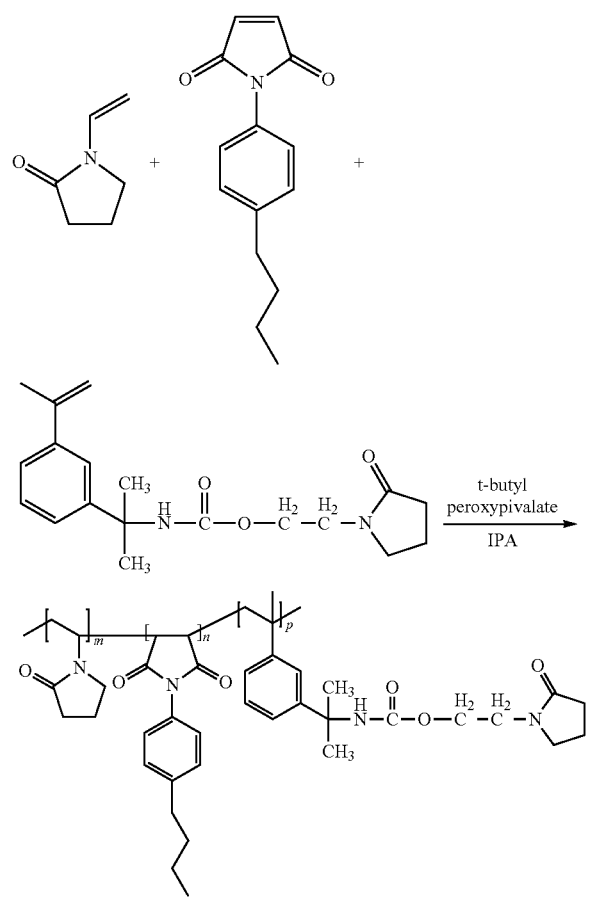

Isopropanol (IPA) (200 g) was charged into to a 1-L round-bottom reaction flask equipped with a nitrogen sparge/sweep, mechanical mixer, charge funnel, and an oil bath with a temperature probe and controller. N-vinyl-2-pyrrolidone (90 g), 4-butylmaleimide (5.0 g), and the high-purity monomer of Example 1 (5.0 g) were added to the flask while maintaining the reaction temperature at 65° C. Tert-butyl peroxypivalate (Trigonox® 25, Akzo Nobel N.V.) copolymerization initiator was added during the course of the synthesis. The reaction temperature was increased to 75° C. and boosters of initiator were added until the residual N-vinyl-2-pyrrolidone monomer level fell below 1000 ppm. As determined by NMR, the polymer contained 94 mol % N-vinyl-2-pyrrolidone, 2 mol % 4-butylmaleimide, and 4 mol % of the monomer from Example 1.

Example 4

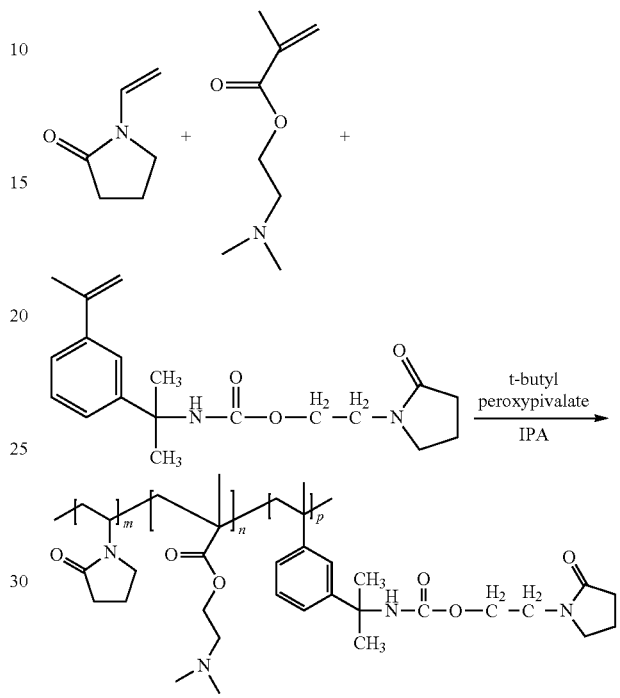

Isopropanol (WA) (200 g) was charged into to a 1-L round-bottom reaction flask equipped with a nitrogen sparge/sweep, mechanical mixer, charge funnel, and an oil bath with a temperature probe and controller. N-vinyl-2-pyrrolidone (76.0 g), dimethylaminoethylmethacrylate (19.0 g), and the high-purity monomer of Example 1 (5.0 g) were added to the flask while maintaining the reaction temperature at 65° C. Tert-butyl peroxypivalate (Trigonox® 25, Akzo Nobel N.V.) copolymerization initiator was added during the course of the synthesis. The reaction temperature was increased to 75° C. and boosters of initiator were added until the residual N-vinyl-2-pyrrolidone monomer level fell below 1000 ppm. As determined by NMR, the polymer contained 85 mol % N-vinyl-2-pyrrolidone, 13 mol % dimethylaminoethylmethacrylate, and 2 mol % of the monomer from Example 1.

The invention has been described in detail with particular reference to preferred embodiments thereof, but it will be understood that variations and modifications can be effected within the spirit and scope of the invention.

What is claimed is:
1. A non-homopolymer derived in part from a monomer represented by the structure:

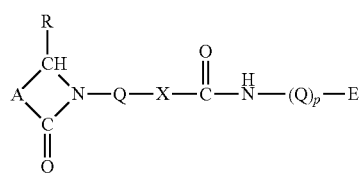

and at least one comonomer, wherein:
A is an alkyl or alkenyl group comprising 2 to 50 carbon atoms, wherein 2 to 4 carbon atoms reside in the lactam ring between the

group and the

group;
E is a polymerizable moiety selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and mixtures thereof;
p is 0 or 1;
Q is independently selected from the group consisting of functionalized and unfunctionalized alkyl, cycloalkyl, alkenyl, and aryl groups, wherein any of the beforementioned groups may be with or without heteroatoms;
R is independently selected from the group consisting of hydrogen, and functionalized and unfunctionalized alkyl, cycloalkyl, alkenyl, and aryl groups, wherein any of the beforementioned groups may be with or without heteroatoms; and
—X— is selected from the group consisting of —O— and

—N—,
 |
 R wherein R retains its definition from this claim;
wherein the non-homopolymer is a random, blocked, or alternating polymer.

2. The non-homopolymer of claim 1 wherein said comonomer is selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl carbonates, vinyl ethers, vinyl imidazoles, vinyl lactams, vinyl pyridines, vinyl silanes, vinyl sulfones, and mixtures thereof.

3. A compound derived from (a) at least one polymer comprising an isocyanate group, and (b) at least one lactam-based molecule represented by the structure:

wherein:
A is an alkyl or alkenyl group comprising 2 to 50 carbon atoms, wherein 2 to 4 carbon atoms reside in the lactam ring between the

group and the

group;
Q is selected from the group consisting of functionalized and unfunctionalized alkyl, cycloalkyl, alkenyl, and aryl groups, wherein any of the beforementioned groups may be with or without heteroatoms;
R is independently selected from the group consisting of hydrogen, and functionalized and unfunctionalized alkyl, cycloalkyl, alkenyl, and aryl groups, wherein any of the beforementioned groups may be with or without heteroatoms; and
—X— is selected from the group consisting of —O— and

wherein R retains its definition from this claim; and
H is a hydrogen atom; wherein the polymer is selected from the group consisting of: poly(neopentyl glycol adipate) polymer terminated with isophorone diisocyanate; poly(phenyl isocyanate-co-formaldehyde); poly(propylene glycol) terminated with 2,4-diisocyanate tolylene; poly(ethylene adipate) terminated with 2,4-diisocyanate tolylene; poly(neopentyl glycol adipate) terminated with isophorone diisocyanate; poly(1,4-butanediol) terminated with 2,4-diisocyanate tolylene; and mixtures thereof.

4. The compound of claim 3 wherein said polymer is a silane isocyanate polymer or a siloxane isocyanate polymer.

5. A non-homopolymer derived in part from a monomer represented by the structure:

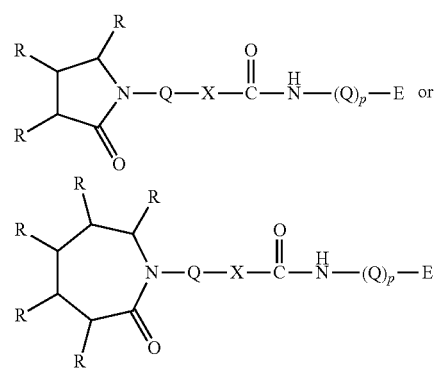

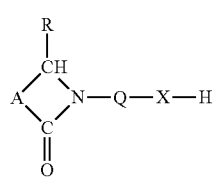

and at least one comonomer, wherein
E is a polymerizable moiety selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and mixtures thereof;
p is 0 or 1;
Q is independently selected from the group consisting of functionalized and unfunctionalized alkyl, cycloalkyl, alkenyl, and aryl groups, wherein any of the aforementioned groups may be with or without heteroatoms;
R is independently selected from the group consisting of hydrogen, and functionalized and unfunctionalized alkyl, cycloalkyl, alkenyl, and aryl groups, wherein any of the beforementioned groups may be with or without heteroatoms; and
—X— is selected from the group consisting of —O— and $$-\overset{R}{\underset{|}{N}}-,$$

wherein R retains its definition from this claim;
wherein the non-homopolymer is a random, blocked, or alternating polymer.

6. The non-homopolymer of claim 5 wherein said comonomer is selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl carbonates, vinyl ethers, vinyl imidazoles, vinyl lactams, vinyl pyridines, vinyl silanes, vinyl sulfones, and mixtures thereof.

7. A compound represented by the structure:

[chemical structure]

wherein
Q is independently selected from the group consisting of functionalized and unfunctionalized alkyl, alkenyl, and alkoxy groups, wherein any of the aforementioned groups may be with or without heteroatoms;
—X— is selected from the group consisting of —O— and $$-\overset{R}{\underset{|}{N}}-;$$

and
R is independently selected from the group consisting of hydrogen, and functionalized and unfunctionalized alkyl, cycloalkyl, alkenyl, and aryl groups, wherein any of the beforementioned groups may be with or without heteroatoms.

8. A homopolymer derived from a monomer represented by the structure:

[chemical structure]

wherein
Q is independently selected from the group consisting of functionalized and unfunctionalized alkyl, alkenyl, and alkoxy groups, wherein any of the aforementioned groups may be with or without heteroatoms;
—X— is selected from the group consisting of —O— and $$-\overset{R}{\underset{|}{N}}-;$$

and
R is independently selected from the group consisting of hydrogen, and functionalized and unfunctionalized alkyl, cycloalkyl, alkenyl, and aryl groups, wherein any of the beforementioned groups may be with or without heteroatoms.

9. A non-homopolymer derived in part from a monomer represented by the structure:

[chemical structure]

and at least one comonomer, wherein
Q is independently selected from the group consisting of functionalized and unfunctionalized alkyl, alkenyl, and alkoxy groups, wherein any of the aforementioned groups may be with or without heteroatoms;

—X— is selected from the group consisting of —O— and

and
R is independently selected from the group consisting of hydrogen, and functionalized and unfunctionalized alkyl, cycloalkyl, alkenyl, and aryl groups, wherein any of the beforementioned groups may be with or without heteroatoms,
wherein said non-homopolymer is a random, blocked, or alternating polymer.

10. The non-homopolymer of claim 9 wherein said comonomer is selected from the group consisting of: acrylamides, acrylates, allyl derivatives, benzoxanes, cinnamyls, epoxies, fumarates, maleates, maleimides, oxazolines, oxetanes, styrenes, vinyl acetates, vinyl acrylamides, vinyl amides, vinyl carbonates, vinyl ethers, vinyl imidazoles, vinyl lactams, vinyl pyridines, vinyl silanes, vinyl sulfones, and mixtures thereof.

* * * * *